(12) United States Patent
Williams, III et al.

(10) Patent No.: US 7,438,727 B2
(45) Date of Patent: Oct. 21, 2008

(54) LOCKING SHOULDER JOINT

(76) Inventors: T. Walley Williams, III, 71 Orchard St., Belmont, MA (US); William J. Hanson, 376 Wataquadock Hill Road, Bolton, MA (US)

(*) Notice: Subject to any disclaimer, the term of this patent is extended or adjusted under 35 U.S.C. 154(b) by 200 days.

(21) Appl. No.: 11/340,925

(22) Filed: Jan. 26, 2006

(65) Prior Publication Data

US 2006/0167562 A1      Jul. 27, 2006

Related U.S. Application Data

(60) Provisional application No. 60/647,844, filed on Jan. 26, 2005.

(51) Int. Cl.
    *A61F 2/66* (2006.01)
(52) U.S. Cl. ...................................................... 623/57
(58) Field of Classification Search ............. 623/57–65
    See application file for complete search history.

(56) References Cited

U.S. PATENT DOCUMENTS 3,382,506 A * 5/1968 Collins et al. ................. 623/60
5,180,086 A * 1/1993 Ikeda ........................... 223/66

* cited by examiner

*Primary Examiner*—Bruce E. Snow
(74) *Attorney, Agent, or Firm*—Brian M. Dingman; Mirick, O'Connell, DeMallie & Lougee

(57) ABSTRACT

A locking shoulder joint adapted to be attached to a user's shoulder, generally comprising a rotor provided with a plurality of radially positioned pins, that rotates relative to a stator, and a cam provided with one or more plungers adapted to engage said rotor pins to releasably lock said rotor in position selected by said user, all of which act to move a humeral member in a direction corresponding to a flexion/extension direction of the shoulder joint; and a yoke coupled to an axle for moving the humeral member in a direction corresponding to an abduction/adduction direction of the shoulder joint.

23 Claims, 7 Drawing Sheets

LOCKING SHOULDER JOINT

CROSS-REFERENCE

This is a continuation in part of U.S. Provisional Patent Application Ser. No. 60/647,844 filed on Jan. 26, 2005.

FIELD OF THE INVENTION

This invention relates to prosthetics and more specifically to a prosthetic shoulder joint.

BACKGROUND OF THE INVENTION

A number of prosthetic shoulder joints have been developed to facilitate shoulder movement in a prosthetic system. These generally consist of two friction joints in close proximity to replace the anatomical motions of flexion-extension and abduction-adduction. The user must overcome this friction to position the joint. When the friction is high, the user requires excessive force to reposition. When it is too low, inadvertent slippage may cause a problem. Furthermore it is impossible to use these joints in the free-swing mode that greatly increases comfort during walking.

Although there are some prosthetic knee joints that provide the user with a free-swing mode in the knee joint, such as those described in U.S. Pat. No. 6,764,520 issued on Jul. 20, 2004 to Deffenbaugh et al., U.S. Pat. No. 4,614,518 issued on Sep. 30, 1986 to Lehneis et al. and U.S. Pat. No. 4,520,512 issued on Jun. 4, 1985 to Lehneis et al., these free-swing knee joints are not suitable for a shoulder joint. The free-swing modes in these prosthetic knee joints are not feasible for use in a shoulder joint because the free-swing mode is either on or off and when on, it is completely free to swing without any intermediary locking positions.

Prior prosthetic shoulder joints also do not provide a means for efficiently managing control cables necessary to activate and control the movements of the prosthesis. Such cables just hang loose and get caught up in or tangled around the prosthesis during movement of the joint.

SUMMARY OF THE INVENTION

It is therefore a primary object of this invention to provide a small, lightweight prosthetic shoulder joint with an adequate range of motion around both axes.

It is a further object of the invention to provide a prosthetic joint with easily adjustable friction about the abduction-adduction axis.

It is a further object of the invention to provide a prosthetic joint with the capability to readily alter the flexion-extension axis between two states-fully locked and free-to-swing.

It is a further object of the invention to provide a prosthetic joint with low friction about the flexion axis when in the free-swing state.

It is a further object of the invention to provide a prosthetic joint with a flexion-extension bearing that can sustain a 50 ft-lb torque about the abduction axis.

It is a further object of the invention to provide a prosthetic joint with a flexion-extension lock that can be operated: manually by reaching over with the sound-side hand to move a knob located on the prosthetic joint; remotely with a chin-activated nudge control (such a control is available as a cable puller with a range of a half inch and with a return spring); remotely with a chest mounted lever (easier to reach than the knob on the prosthetic joint); or remotely by using a solenoid or other electric actuator.

It is a further object of the invention to provide a prosthetic joint with a flexion-extension lock that will not unlock due to load until the unlocking mechanism is activated.

It is a further object of the invention to provide a prosthetic joint wherein the unlocking mechanism can be actuated while there is a moderate load about the axis.

It is a further object of the invention to provide a prosthetic joint wherein the lock may auto-engage at the next lock position after the user sets the mechanism into its locked state.

It is a further object of the invention to provide a prosthetic joint with a flexion-extension lock with multiple locking positions.

It is a further object of the invention to provide a prosthetic joint with a flexion-extension lock that can sustain at least 50 ft-lb of torque.

It is a further object of the invention to provide a prosthetic joint with a joint mechanism that will operate for multiple years without substantial wear.

It is a further object of the invention to provide a prosthetic joint with a means for passing wires through or very near the joint axes. For example, for connectors to pass through, holes of ½ inch diameter are typically required.

A preferred embodiment of the locking shoulder joint of the invention, for use with a prosthesis, generally comprises: a rotor having an axis of rotation and provided with a plurality of rotor pin holes in the rotor that are spaced equidistant from each other with a corresponding number of rotor pins fixed in the pin holes wherein at least a portion of the pins extends out from the pin holes to define a plurality of spaces between pins; a cam provided with one or more plungers having an outer dimension that is adapted to releasably engage the spaces between the pins; a stator; a means for enabling the rotor to rotate relative to the stator; a means for activating the rotor to rotate relative to the stator; and a means for fixing the stator to the prosthesis.

The means for enabling the rotor to rotate may comprise at least two ball races and a plurality of bearing balls in the ball races located between the rotor and the stator, wherein the ball races are preferably a groove in a surface of the rotor adjacent to the stator.

The shoulder joint preferably comprises six pins for every one plunger. For example, when the rotor is able to rotate 360 degrees about the axis of rotation, the rotor preferably comprises thirty-six pins positioned at 10 degree intervals about the axis of the rotor, and the cam would then preferably comprise six plungers.

The cam is preferably a cam ring, and the stator is optimally positioned between the rotor and the cam ring, wherein the stator comprises a bore, corresponding to the plunger, through which a plunger pin is provided, and wherein the plunger pin is fixed to the cam ring proximate one end of the plunger pin and is fixed to the plunger proximate an opposite end of the plunger pin.

The means for activating the rotor to rotate relative to the stator may comprise an alternator member, wherein the alternator member may further comprise, puller engagingly attached to the cam; and an alternator plate fixed to the stator, wherein the puller is preferably positioned between the stator and the alternator plate.

When the axis of rotation of the rotor is in a direction corresponding to a flexion/extension of the shoulder joint, the shoulder joint may further comprise a means for moving the shoulder joint in an abduction/adduction direction, wherein the means for moving the shoulder joint in an abduction/adduction direction may comprise, an axle having an axis of rotation substantially perpendicular to the axis of rotation of the rotor; a means for fixing the axle to the rotor; a yoke member having a bore in which the axle rotates so that the yoke member is adapted to move in a direction corresponding to an abduction/adduction direction of the shoulder joint.

Another embodiment of the locking shoulder joint of the invention that is adapted to be attached to a user's shoulder, generally comprises, a humeral member; a means for moving the humeral member in a direction corresponding to an abduction/adduction direction of the shoulder joint; a means for moving the humeral member in a direction corresponding to a flexion/extension direction of the shoulder joint; and a means for indirectly attaching the humeral member to the user's shoulder. The means for moving the humeral member in a direction corresponding to an flexion/extension direction of the shoulder joint preferably comprises, a rotor having an axis of rotation and provided with a plurality of rotor pin holes in the rotor that are spaced equidistant from each other with a corresponding number of rotor pins fixed in the pin holes wherein at least a portion of the pins extends out from the pin holes to define a plurality of spaces between pins; a cam provided with one or more plungers having an outer dimension that is adapted to releasably engage the spaces between the pins; and a stator. The means for moving the humeral member in a direction corresponding to an abduction/adduction direction of the shoulder joint preferably comprises, an axle having an axis of rotation substantially perpendicular to the axis of rotation of the rotor; a means for fixing the axle to the rotor; a yoke member having a bore in which the axle rotates so that the yoke member is adapted to move in a direction corresponding to an abduction/adduction direction of the shoulder joint.

The shoulder joint may still further comprise an alternator member that comprises, a puller engagingly attached to the cam; and an alternator plate fixed to the stator, wherein the puller is between the stator and the alternator plate.

As with all of the embodiments, the shoulder may still further comprise a bore through the rotor, the stator, the cam, and the alternator plate through which one or more control cables may be passed.

Another embodiment of the locking shoulder joint of the invention for use with a prosthesis, generally comprises, a rotor having an axis of rotation and provided with a plurality of rotor pin holes in the rotor that are spaced equidistant from each other with a corresponding number of rotor pins fixed in the pin holes wherein at least a portion of the pins extends out from the pin holes to define a plurality of spaces between pins; a cam provided with one or more plungers having an outer dimension that is adapted to releasably engage the spaces between the pins; a stator; a means for enabling the rotor to rotate relative to the stator; a means for activating the rotor to rotate relative to the stator; and a means for fixing the stator to the prosthesis; and wherein a passageway extends through the rotor, the stator and the cam, through which one or more control cables are passed. The passageway is an opening through the rotor, the stator, the cam and the alternator plate extending generally along the axis of rotation of the rotor.

The locking shoulder joint components are preferably made from high-strength aerospace-quality alloys such as aircraft aluminum and then coated with a hard anodizing material. Locking pins and plungers are made of hardened, non-corrosive steel. The extension/flexion components allow the shoulder to swing in a natural arc when the user is walking yet can be locked in 36 positions. A second hinge member that utilizes adjustable friction enables the user to move the shoulder in an abduction/adduction direction. When free, the joint moves in flexion/extension so easily that a bilateral amputee may reposition an entire arm by merely leaning forward while pushing a lock release. The size and weight of the joint make it suitable for pediatric use although it is designed to bear the loads imposed by an adult. An optional powered lock/unlock mechanism is provided.

The locking shoulder joint may be adapted for either an exoskeletal or endoskeletal application. The exoskeletal version may comprise a humeral mounting plate. The endoskeletal version utilizes an adapter tube and a clamp. The joint is preferably attached to the socket with a mounting ring or, if the socket will not support the joint, a three-spoke mounting plate may be used to provide exceptional strength and stability to the joint.

The joint may be controlled in a number of ways: it may be activated directly by a knob mounted on the puller or by a cable to a remote lever. Alternatively, a remote lever-actuated release may be mounted in a convenient location for the user to reach. The cable may be pulled by a chin-activated lever or chest-mounted lever pulling the cable in a Bowden sheath. Finally, the locking mechanism may be controlled with a powered actuator either directly or remotely. A powered locking mechanism may be operated with a touch pad, myoelectrode or switch.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

Figure 1:
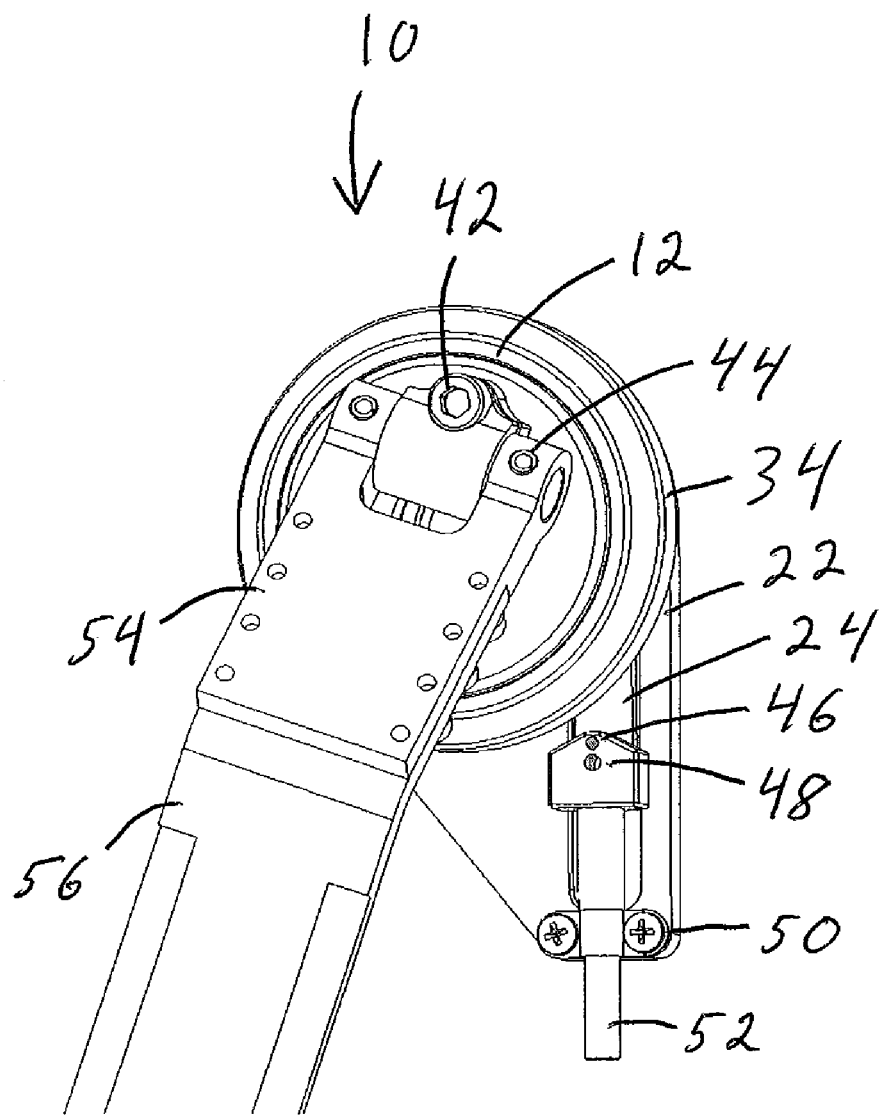
FIG. 1 is a perspective view of the preferred embodiment of the shoulder joint of the invention.

The invention features a prosthetic shoulder joint that preferably locks in 36 positions, or every 10 degrees. This resolution is preferred to allow the user to position the limb as needed. The user can trip the lock mechanism even when the locking plungers are not lined up, and as soon as the joint reaches the nearest 10° position, the lock auto-engages. There is no need to pre-align the locking components manually, thus making it easier to engage the lock. Additionally, the joint can be unlocked under a moderate load, a feature seldom found in locking prosthetic joints.

The lock may easily be engaged or disengaged with a manual lever actuator. Alternatively, the lock may be actuated using a remote mechanical or an electric actuator. Remote actuation is needed when the user cannot access the lock release mechanism directly. For example, a bilateral amputee would benefit from the optional electric actuator.

An alternator mechanism activates the lock. Thus, only pull actions are required rather than push-pull. Most of the actuators used in prosthetics operate by pulling with a cable. The alternator permits a pull-only cable to both lock and unlock the joint and allows the flexion-extension joint to be left in either the locked or free-swing state. Furthermore, it permits a simple solenoid to be used as the electric actuator. Alternating actuation simplifies the operation of the lock for the user.

The joint described is preferably about 2.4 inches in diameter. It protrudes less than 1.4 inches at the flex-extension rotation axis, and the weight with the complete unlocking mechanism is less than 150 grams. As shown in the Figures, the device of the invention is generally shown and referred to as locking shoulder joint 10. Locking shoulder joint 10 generally comprises a rotor 12 with rotor pins 17, rotor balls 14, stator 16, plungers 18, plunger pins 20, cam ring 21 (clutch plate), cam-puller pin 23, puller 24, follower or puller spring 40, and alternator plate 22. In addition, mounted on rotor 12 are yoke axle 58, yoke axle liner or bushing 60, yoke 54, and humeral plate 56.

The member attached to the user prosthesis is stator 16 that has an inner stator portion 16B and an outer stator portion 16A. The member that attaches to the prosthetic upper arm comprises two submembers that rotate about two axes that perpendicular to each other but the two rotating submembers do not need to intersect. The first rotating member is the flexion and extension axis member referred to herein as rotor 12. The second rotating member is the abduction/adduction axis member referred to herein as yoke 54. Yoke 54 is preferably is mounted on rotor 12 as shown in FIGS. 1, 2, 3 and 4. Yoke 54 attaches to the user's upper arm via humeral plate 56. In the embodiment shown the figures, the abduction/adduction axis comprises an adjustable friction clamp. Other embodiments may have a low-friction bearing to enable the abduction/adduction motion to compensate for gravitational loads. The position of the friction clamp may be locked as desired with a means for locking.

Figure 3:
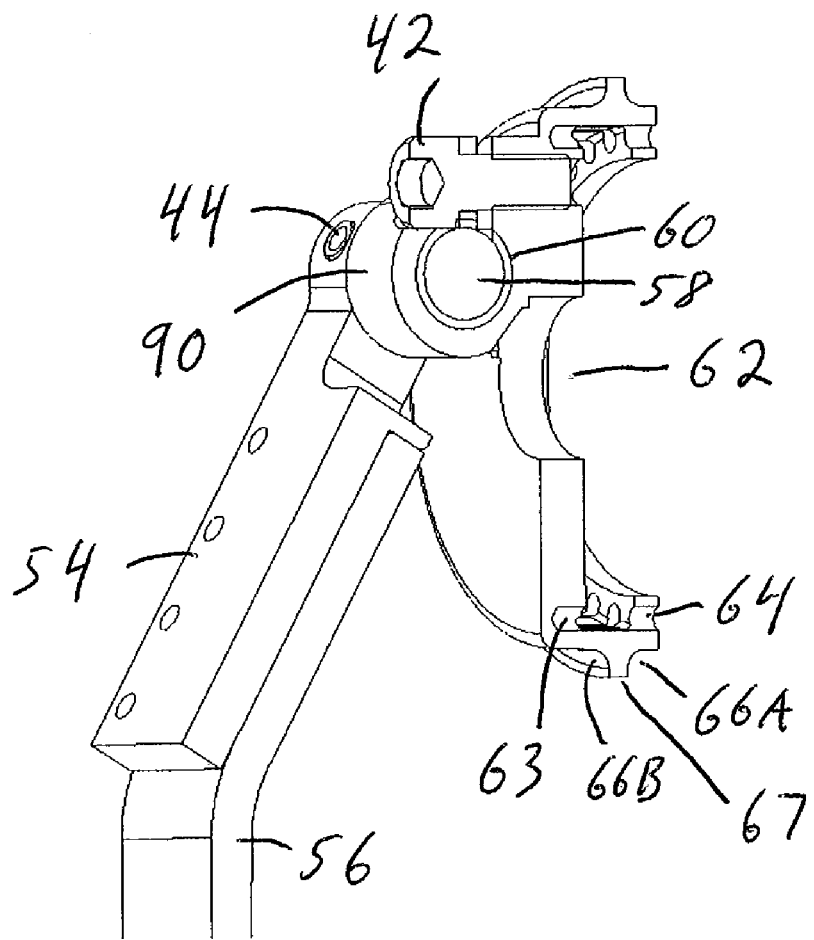
FIG. 3 is a partial cross-sectional view of the rotor of the preferred embodiment with attachments.
Figure 4:
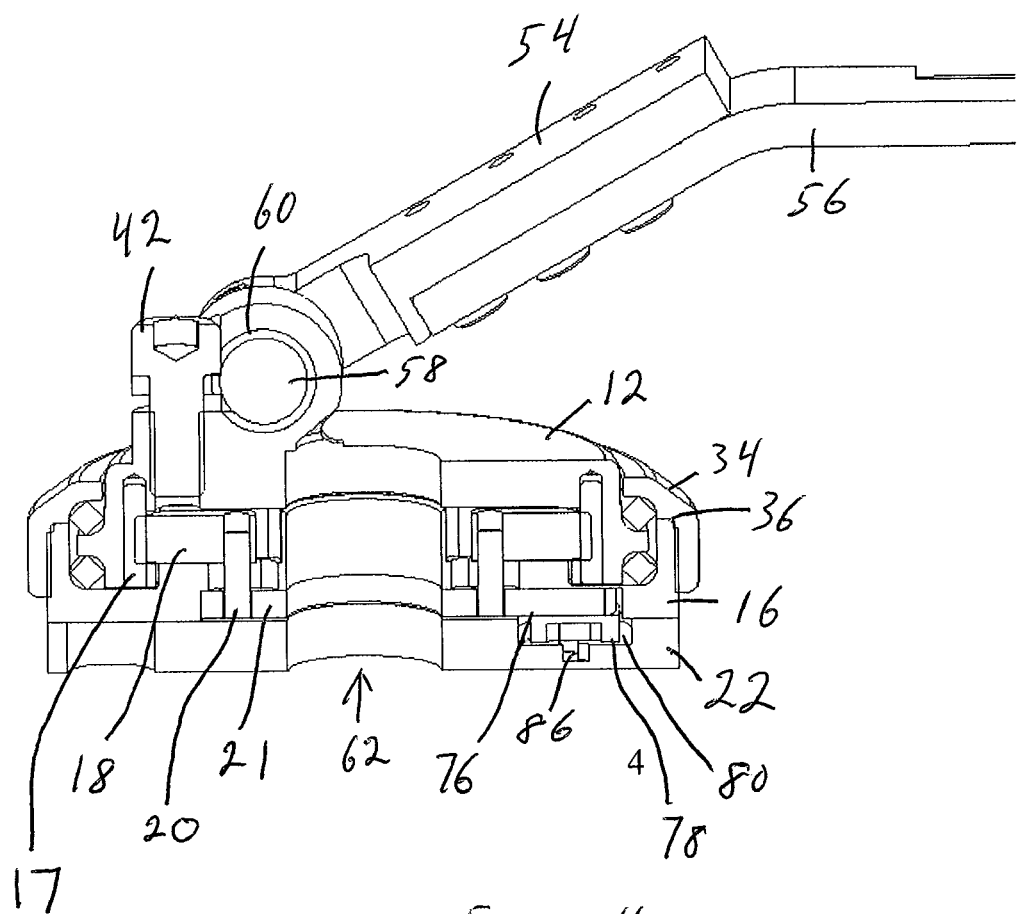
FIG. 4 is a partial cross-sectional view of the preferred embodiment of the shoulder joint of the invention.
Figure 5:
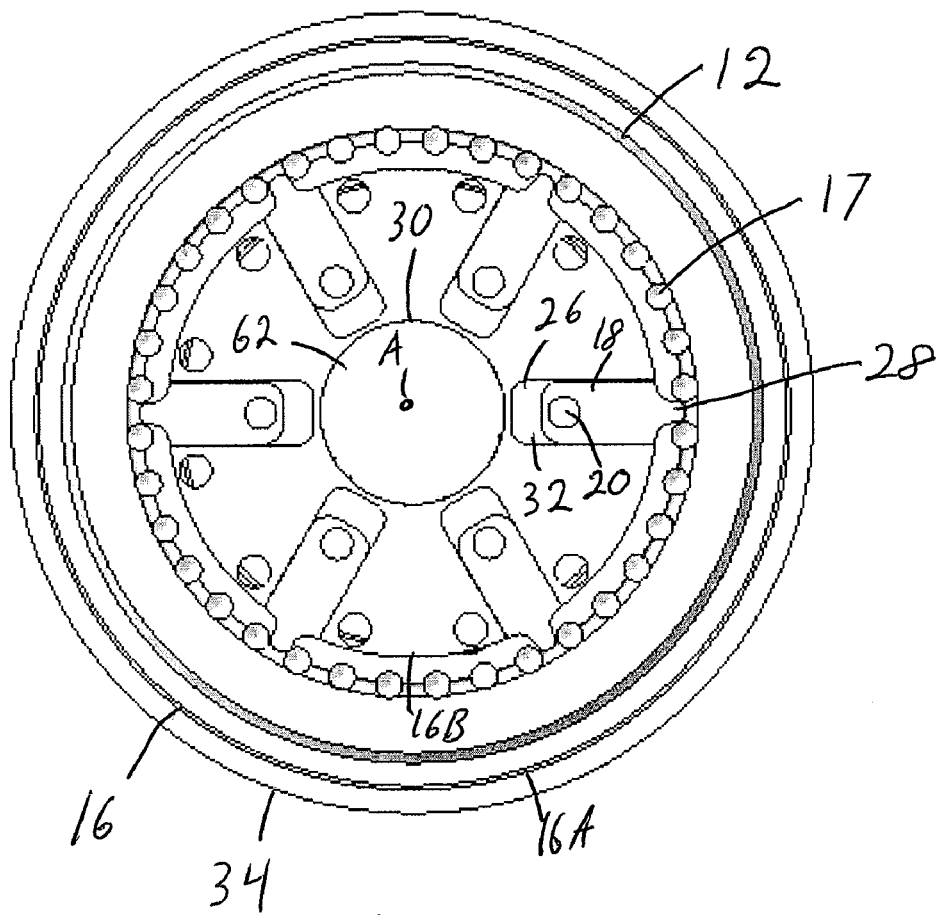
FIG. 5 is a cross-sectional view of the rotor-stator assembly of the preferred embodiment of the invention.

As shown in FIG. 3, rotor 12 has a flange 67 on its outer circumference that defines races 66A and 66B along which a series of balls 14 (represented in FIG. 4 as diamond toroids) on both sides of flange 67. On the user side, the balls contact a circumferential race 66A that is part of stator 16. On the other side, the balls contact a circumferential race 66B in a cap or housing ring 34 that screws via thread 36 onto stator 16. When cap ring 34 is in place, it closes any gaps so that the rotor 12 is fully constrained against all motions except rotation about axis A running through the center as shown in FIG. 5.

The center of rotor 12 is hollow, having a hole 62 (FIGS. 3 and 5) large enough through which wires and connectors may be passed. Hole 62 provides a wireway through the device. The non-user side of the rotor is thick enough to mount the abduction axis component that is preferably an integral part thereof. The abduction axis mount including yoke 54 (FIGS. 1 and 4) is offset from the flex-extend axis far enough to accommodate the central wire-pass-through hole. On the user side, additional material is removed from the center of rotor 12 until only a thick annular housing ring 34 is left supporting the ball-race flange 67. A groove 63 is provided on the inside of the thick annular ring. On the user side, the ring is pierced with a plurality of holes 64 parallel to the rotation axis. These holes intersect groove 63 above.

As noted, in the preferred embodiment, there are 36 holes, 10° apart, into which hardened steel rotor pins 17 are force fit. These pins form the locking components of the rotor 12. The stator 16 protrudes inside the central portion of the rotor 12 with a wire-pass-through hole in the center. As shown in FIG. 4, stator 16 protrudes as far as the nonuser side of groove 63 in the rotor 12 with the installed pins 16. As shown in FIG. 5, six parallel-side channels or slots 26 are machined into the nonuser side of stator 16 so six sliding plungers 18 can be driven outward to slide between pairs of rotor pins 17. The engaging ends of the plungers referred to as plunger noses 28 may be slightly tapered at their outmost ends where they slide between rotor pins 17. The noses 28 are cylindrical so that they will always seek to slide between pins 17 when engaging without catching or otherwise getting hung up on any edges. Each plunger has a plunger pin on the opposite end of noses 28 that is adapted to engage plunger pin slot 32.

Figure 6:
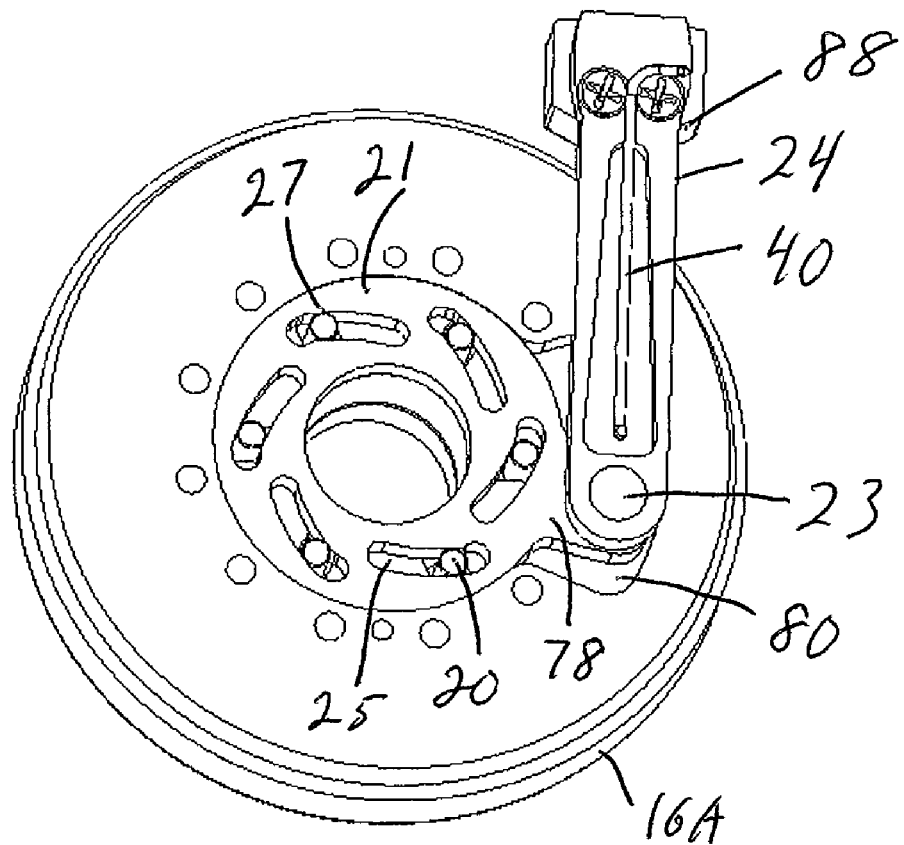
FIG. 6 is a perspective view of the stator and puller assembly of the preferred embodiment of the invention.

A thin cylindrical cam ring pocket 76 is provided on the user side of stator 16 to accommodate cam ring 21 which has six spiral grooves 25, also referred to as cam slots, that act as cams. A layer of metal is provided between cam ring 21 and the surface on which plungers 18 slide. The six holes or slots 25 connect these two elements so that plunger pins 20, that are force fit into plungers 18, can pass through into spiral grooves 25 as shown in FIG. 6. Each slot has an over-center point 27. When cam ring 21 rotates, it drives plunger pins 20 and therefore plungers 18 either outward to engage the 36 rotor pins or inward so that rotor 12 is free to rotate. To rotate cam ring 21, a thin protrusion 78 is provided. The protrusion 78 moves in a pocket 80 that is about 60° wide. This pocket is an extension of the cam ring pocket 76. Pocket 76 is deep enough so that cam ring 21 is free to move after alternator plate 22 is fixed to the user side of stator 16. Alternator plate 22 retains cam ring 21 in pocket 76. It also has clearance holes 82 for screws that attach stator 16 to the prosthesis (not shown) and a central wire-clearance hole. Two countersunk screws 74 hold alternator plate 22 to stator 16. As shown in FIG. 4, alternator plate 22 extends beyond the outside diameter of stator 16 on one side. This extension contains an elongated pocket 86 that passes under the pocket 80 in stator 16 that accommodates protrusion 78 on cam ring 21.

A puller 24 moves in pocket 86. The end of puller 24 under cam ring protrusion 78 couples to protrusion 78 by means of cam puller pin 23 that passes through both members. Thus, when puller 24 is moved in pocket 86, it causes cam ring 21 to rotate. The end of puller 24, opposite from cam ring-puller pin 23, projects above the surface of alternator plate 22 to provide a protruding structure 88 for attaching an actuation cable sheathed in a Bowden cable sheath 52, as shown in FIG. 1, for remote operation or optionally a simple knob fixed in knob hole 48 for manual operation. The actuation cable slides within a Teflon™-lined spring sheath 52 affixed to the alternator plate by clamp 50. A setscrew 46 may be used to clamp the cable to the housing.

To move cam ring 21 in the opposite rotational direction, return or follower spring 40, that is concentric with the cable, is provided and fixed in a pocket on puller 24. Spring 40 slides over the end of the spring sheath and butts up against clamp 50 that holds sheath 52. Screws 68 are used to hold spring 40 is place.

Depending on the user, the cable may be pulled by a remote lever to activate the lock mechanism, while spring 40 reengages the lock. For users needing free swing however, the alternator feature described above must be incorporated into the basic mechanical assembly. As noted, the first element of the alternator is the follower spring mounted in an elongated pocket in the Puller. A nib on the end of this spring pushes down against the floor of the pocket 80 in alternator plate 22. The second element of the alternator is the cam path in the floor of the pocket in the alternator plate. This path may vary in height and provides for motion of the nib along one path when cable in cable sheath 52 pulls the puller 24. Relaxing the cable then permits the nib to partially return while it moves sideways into a meta-stable recess. A further pull moves the nib further sideways into a second path. Releasing the cable tension lets the puller return all the way to the fully locked position where the nib "falls" into the original path ready to repeat the action. This alternator is of the classic ballpoint pen mechanism design in a flat plane.

Figure 7:
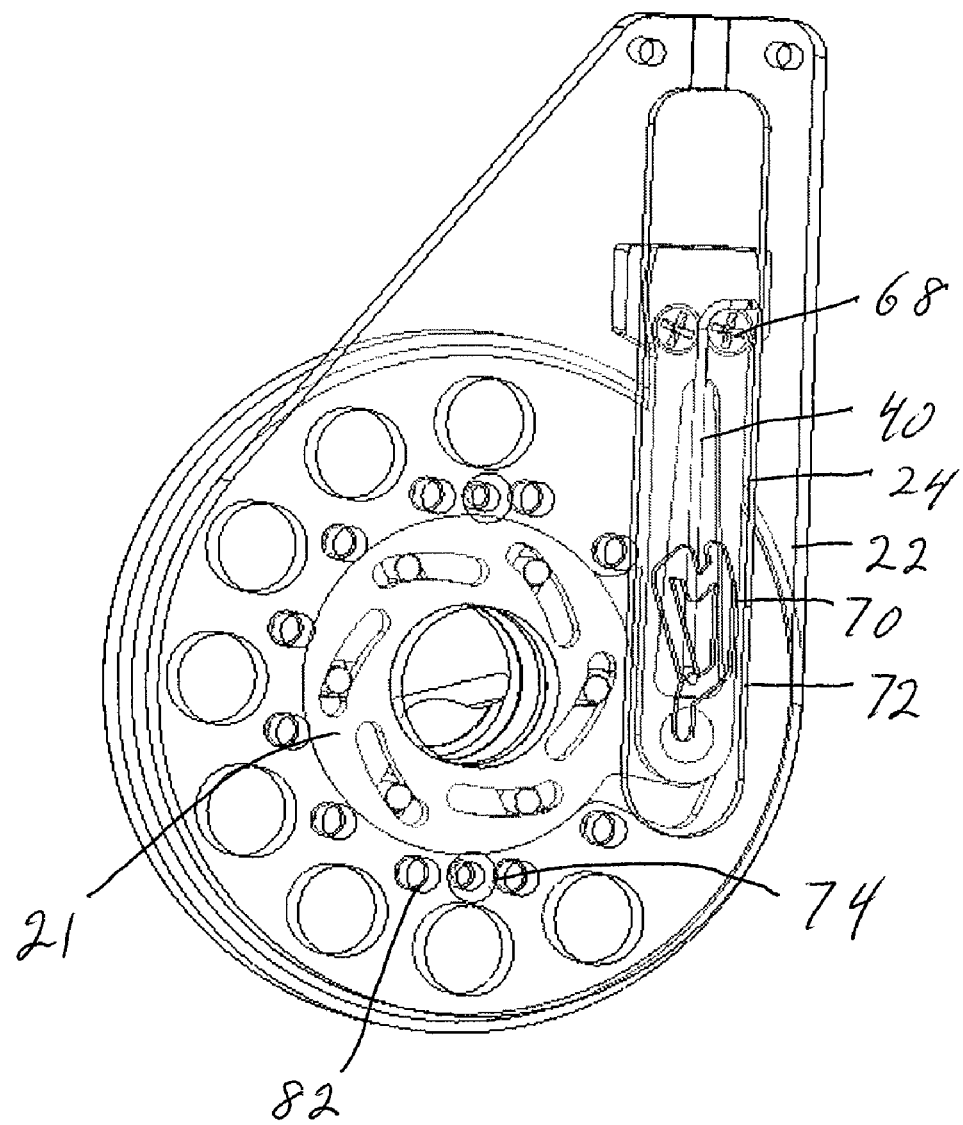
FIG. 7 is a perspective view of the stator and puller assembly shown in FIG. 6 with the alternator plate.

The entire unit is attached to the user's prosthetic interface or socket by a mounting ring on the inside of the interface with multiple screws passing through the interface and the alternator plate into tapped holes in stator 16 as shown in FIG. 7. The locking action of the shoulder joint occurs when the six plungers 18 move outward in slots 26 in stator 16 to jam between pairs of rotor pins 17 in rotor 12 thus coupling rotor 12 to stator 16. Plungers 18 are moved outward by plunger pins 20 that are cammed in or out by rotating cam ring 21. As this ring is rotated clockwise, it moves the 1, 2, 3 through 6 plungers toward the outer circumference of the joint. These plungers then engage the fixed rotor pins 17, thus locking the shoulder joint and preventing rotor 12 from turning. Releasing the lock is achieved by reversing this process and rotating cam ring 21 in the opposite direction counter clockwise. As soon as plungers 18 disengage and clear rotor pins 17, the joint is free to rotate again. The joint can be left in either the locked or unlocked position.

As noted, to reduce friction and facilitate true "free swing," the joint is provided with two ball-bearing raceways 66A and 66B. These raceways are positioned toward the outer circumference of the joint to provide adequate support for the relatively high off-axis torque loads on the joint. The relatively large number of bearing balls 14 is used to help distribute these torque loads without causing damage to the bearing surfaces. In an alternate mounting arrangement, the joint is attached to a metal plate with multiple bands.

Figure 2:
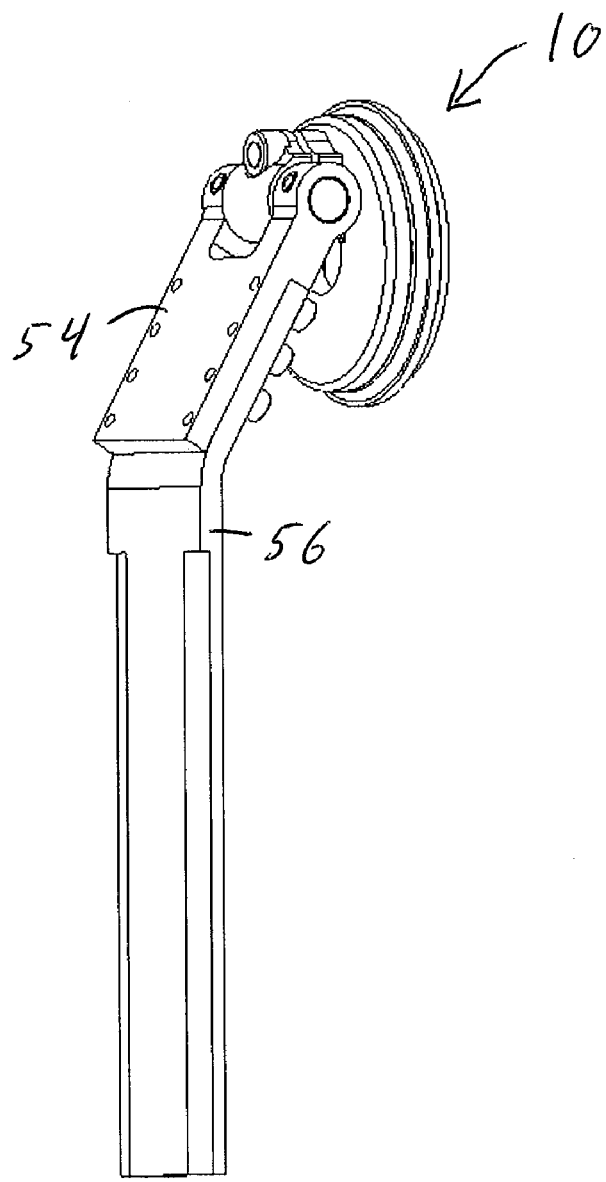
FIG. 2 is a perspective view of the rotor of the preferred embodiment with the yoke and humeral plate attached.

The joint is attached to the prosthetic socket with a mounting plate. The prosthetic system is then attached to the shoulder joint by humeral plate 56. As shown in FIG. 2, rotor 12 is shown with its attached yoke 54 and humeral plate 56. The orientation illustrated is the preferred orientation when applying the joint to a user.

In an alternate mounting arrangement, the joint is attached to a metal plate containing multiple strips. These strips are bent and formed by the prosthesis technician. This arrangement is often used for temporary fittings while the user's wounds are healing or while the permanent prosthesis is being fabricated.

The shoulder joint preferably provides a locking action in which multiple parallel rotor pins are spaced equally around the rotation axis. Sliding plungers move in slots in a fixed stator element and pass between the rotor pins to prevent rotation. The uniqueness of this joint design is the way the structures are disposed so that they accommodate the design constraints. The rotor pins used in this joint are hardened pins parallel to the joint axis.

As noted, the shoulder joint preferably locks approximately every 10 degrees by utilizing 36 pins. To accommodate the large torque load, multiple plungers are needed to interact with the pins. Although the number of pins and the number of degrees between the pins may be varied, other variations include, but are not limited to: 30 pins at 12° intervals, 32 pins at 11.25° intervals, 36 pins at 10° intervals, and 40 pins at 9° intervals. However, as the number of pins increases, the structure as a whole, increases in size which decreases the desirability and practical functionality of the device. Thirty-six pins are preferred in part because the number is divisible by six, thus permitting six plungers to share the load and allowing a cam ring to readily fit into the available space.

The diameter of the joint should remain small, preferably no greater than 2½ inches or less and the flex-extension bearing preferably accommodates a high cross torque. As such, the plungers engage the rotor pins from the inside and the ball race is located as far out as possible from the locking mechanism. There is generally no room for commercial ball bearing assemblies. The races should be loaded as full as possible minus one ball. Because rotation is slow, the inter-ball friction can be ignored. For adequately reduced friction, ball races are preferred. These races use relatively small balls without separators because the speed of rotation is low. Full races spread the cross-torque loads out better than separated balls. The bearing surfaces preferably comprise ultra-high strength aluminum.

The pins and plungers also must be sufficiently hard so that minimal wear will occur during lock and unlock under the design loads. Parallel-to-the-axis, hardened pins are preferably used for the locking elements in the rotor. By using hard, replaceable pins, the rotor itself is then preferably made of lighter aluminum alloy. The pins are supported on both ends by the material of the rotor, while the active portion of each pin is within a machined-out groove. Likewise, the adjustable-friction abduction-adduction bearing requires long life, which is achieved by adding a bushing 60 between the yoke axle 58 and the wrap around 90 on the rotor, which is typically an area of excessive wear. Spring pin 44 holds yoke 54 to axle 58. A friction screw 42 is used to hold wrap around 90 against the outer face of rotor 12. Together, yoke 54, which is attached to axle 58 with spring pin 44 enable the user to rotate the humeral plate 56, which is attached to a prosthetic arm (not shown), in an abduction/adduction direction.

The abduction-adduction joint should also accommodate a static torque of 50 ft-lb and sudden shock loads. As noted, to do so, multi-turn spring pins 44 are used to couple yoke 54 to yoke axle 58. With reference to FIG. 3, rotor 12 is shown with its attached structures. The friction screw tightens the wrap-around 90 portion of rotor 12, which in turn squeezes bushing 60 against axle 58 to which yoke 54 is attached. This bushing prevents wear and may be oil-impregnated.

An important feature of the joint is the large diameter hole for passing wires and connectors. The wires almost pass through both axes, which will prevent pulling of the wires with rotation about either axis. A bend provided in humeral plate 56 places the plate in a position so that it aligns with the lateral wall of a typical exoskeletal upper arm shell.

The cam grooves may be simple arcs that engage the plunger pins when the cam rotates. In this embodiment, the leading ends of the plungers are parallel and just fit between the rotator pins. There is no back-drive of the plungers in this embodiment and the withdrawal of the plungers require more force than a version with tapered surfaces on the leading ends of the plungers.

The device should also allow a user to set the lock when the plungers are between the exact lock positions of the rotor pins. To do so, the return spring 40 is provided to push the puller 24 in the direction that engages the locking action. When any of several actions move the puller 24 toward spring 40, the plungers disengage. The spring always acts to relock the joint except when the alternator feature keeps the puller from returning.

The lock also preferably engages and disengages by a cable that only applies force in one direction. This is achieved by using the alternator mechanism described above. In the preferred embodiment described, the alternate action is provided using the follower spring 40 with a nib that runs into a cam groove. The groove preferably changes height abruptly to guide the nib into two stable positions similar to the mechanism used in ballpoint pens and push-pull switches. The plungers and the cams driving them have sufficient extra travel so that the cable can pull the nib past the position where it will go into its stable unlocked position.

Although the locking action occurs in the center of the joint, it should be activated from the periphery without adding excessive height to the assembly. As such, the preferred embodiment is provided with the shallow recess 78 in the stator on the side opposite the plungers. To get the motion to the outside, shallow pocket 78 is provided to accommodate the extension on cam ring. Facing this pocket is pocket 80 in the alternator plate that accommodates puller 24. As shown in FIG. 1, when the cable inside the Bowden sheath is pulled, it moves the puller to unlock the joint. Release of the cable leaves the puller in the unlock position. A second pull disengages the alternator mechanism under the puller so that the spring can move the puller the other way to engage the lock.

As shown in FIG. 4, rotating cam ring 21 moves plunger pins 20 and plungers 18 toward the center or outward. The joint locks as the plungers pass between the rotor pins 28. The plungers are constrained to move in and out, driven by the plunger pins. As shown in FIG. 5, the plungers are in the outer or locked position between the rotor pins. Plungers 18 are driven inward by the plunger pins, which are driven inward, in turn, by cam ring 21 hidden below stator 16.

As shown in FIG. 6, cam ring 21 and the boss on one side of it are recessed into the bottom of stator 16. Puller 24 below it, is flush with the surface of the bottom of stator 16. When puller 24 is moved, cam-puller pin 23 moves cam ring 21 to move the plunger pins in and out. As shown in FIG. 7, the alternator plate 22 (clamp plate) is below the stator in phantom.

Those skilled in the art will recognize that the locking joint of the invention may be readily adapted for use in any other prosthetic or orthotic joint applications. For example, the joint of the invention is particularly suited for use in joints requiring a locking mechanism such as wrist, elbow or humeral rotator joints.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A locking prosthetic joint, comprising:
  a stator;
  a rotor adapted to rotate relative to said stator about an axis of rotation, and comprising a plurality of structures essentially regularly spaced around said axis of rotation to define a plurality of spaces between said structures;
  one or more plungers adapted to releasably engage the spaces between the structures; and
  a device comprising a cam ring, and a plunger pin coupled to the plunger for moving said plungers from an outward locking position in which one or more plungers are at least in part located in a said space between two of said structures to prevent said rotor from rotating relative to said stator, and an inward free position in which said one or more plungers are free from said structures to allow said rotor to rotate relative to said stator.

2. The joint of claim 1 further comprising at least one ball race and a plurality of bearing balls in said ball race located between said rotor and said stator.

3. The joint of claim 2 wherein a said ball race comprises a groove in a surface of said rotor adjacent to said stator.

4. The joint of claim 1, wherein said rotor is free to rotate 360 degrees about said axis and wherein said structures comprise pins, and wherein said rotor comprises thirty-six pins positioned at about 10 degree intervals about said axis of rotation.

5. The joint of claim 4 comprising six plungers.

6. The joint of claim 1, wherein said cam ring defines one or more arc-shaped slots, and wherein each said plunger pin rides in one slot.

7. The joint of claim 1, wherein said stator comprises a bore, corresponding to a said plunger, through which said plunger pin is provided, and wherein said plunger pin is engaged with said cam ring proximate one end of said plunger pin and is fixed to said plunger proximate an opposite end of said plunger pin.

8. The joint of claim 1, wherein said device for moving said plungers comprises an alternator member.

9. The joint of claim 8, wherein said alternator member comprises a puller coupled to said one or more plungers.

10. The joint of claim 9, wherein said alternator member further comprises a follower spring with a nib that is guided into two different stable positions.

11. The joint of claim 1, wherein said axis of rotation is in a direction corresponding to a flexion/extension of said joint, and the locking joint further comprises a device for allowing movement of said joint in an abduction/adduction direction.

12. The joint of claim 11, wherein said device for allowing movement of said joint in an abduction/adduction direction comprises:
  an axle having a longitudinal axis that is substantially perpendicular to said axis of rotation;
  structure that couples said axle to said rotor; and
  a yoke member defining a bore in which said axle is at least in part located so that said yoke member is adapted to be rotated about said longitudinal axis of said axle in a direction corresponding to an abduction/adduction direction of said joint.

13. The joint of claim 1, wherein said rotor defines a generally round circumference, said structures are located near said circumference, and in said inward free position said plungers are located inside of said structures toward said axis of rotation, such that said plungers move between two said structures from the inside of said structures when said plungers move from said inward free to said outward locking position.

14. The joint of claim 1, wherein said structures comprise pins that are generally parallel to said axis of rotation.

15. The joint of claim 14, wherein said pins are supported proximate both ends by said rotor, and between said ends overly a groove in said rotor.

16. The joint of claim 1, further comprising a bore through said rotor and said stator located along said axis of rotation.

17. The joint of claim 1, wherein said plungers are normally in said locked position.

18. The joint of claim 1, further comprising a plurality of pin holes in said rotor that are spaced equidistant from each other, and said structures comprise pins fixed in said pin holes.

19. The joint of claim 1, further comprising a device that sets said plungers to lock by moving from said free position to said locking position, and that sets said plungers to unlock by moving from said locking position to said free position, in which said plungers can be set to lock or unlock regardless of their current position relative to said structures.

20. The joint of claim 1, wherein said plungers define tapered ends that enter and leave said spaces between said structures.

21. The joint of claim 20, wherein said tapered ends are cylindrical.

22. A locking prosthetic joint, comprising:

a stator;

a rotor adapted to rotate relative to said stator about an axis of rotation that is in a direction corresponding to a flexion/extension of said joint, said rotor comprising a plurality of structures spaced around said axis of rotation to define a plurality of spaces between said structures;

a plurality of plungers that are sized to at least in part fit in the spaces between said structures;

a device for moving said plungers from a locking position in which said plungers are at least in part located in a said space between two of said structures to prevent said rotor from rotating relative to said stator, and a free position in which said one plungers are free from said structures to allow said rotor to rotate relative to said stator;

an axle having a longitudinal axis that is substantially perpendicular to said axis of rotation;

structure that couples said axle to said rotor; and a yoke member defining a bore in which said axle is at least in part located so that said yoke member is adapted to be rotated about said longitudinal axis of said axle in a direction corresponding to an abduction/adduction direction of said joint.

23. A locking prosthetic joint, comprising:

a stator;

a rotor adapted to rotate relative to said stator about an axis of rotation that is in a direction corresponding to a flexion/extension of said joint, said rotor comprising a plurality of pins spaced around said axis of rotation to define a plurality of spaces between said pins;

a plurality of plungers that are sized to at least in part fit in the spaces between said pins;

a device for moving said plungers from a locking position in which said plungers are at least in part located in a said space between two of said pins to prevent said rotor from rotating relative to said stator, and a free position in which said one or more plungers are free from said pins to allow said rotor to rotate relative to said stator, said device for moving said plungers comprising a structure that defines a plurality of arc-shaped slots, and wherein each said plunger comprises a pin that rides in one slot;

an axle having a longitudinal axis that is substantially perpendicular to said axis of rotation;

structure that couples said axle to said rotor; and a yoke member defining a bore in which said axle is at least in part located so that said yoke member is adapted to be rotated about said longitudinal axis of said axle in a direction corresponding to an abduction/adduction direction of said joint.

* * * * *